(12) United States Patent
Toppinen

(10) Patent No.: US 9,914,714 B2
(45) Date of Patent: Mar. 13, 2018

(54) SELECTIVE PROCESS FOR CONVERSION OF LEVULINIC ACID TO GAMMAVALEROLACTONE

(71) Applicant: Neste Oyj, Espoo (FI)

(72) Inventor: Sami Toppinen, Espoo (FI)

(73) Assignee: NESTE OY J, Espoo (FI)

( * ) Notice: Subject to any disclaimer, the term of this patent is extended or adjusted under 35 U.S.C. 154(b) by 2 days.

(21) Appl. No.: 15/388,924

(22) Filed: Dec. 22, 2016

(65) Prior Publication Data

US 2017/0183321 A1 Jun. 29, 2017

(30) Foreign Application Priority Data

Dec. 23, 2015 (FI) ..................................... 20156006

(51) Int. Cl.
| C07D 307/33 | (2006.01) |
| C07D 307/32 | (2006.01) |
| C07C 51/367 | (2006.01) |

(52) U.S. Cl.
CPC .......... *C07D 307/33* (2013.01); *C07C 51/367* (2013.01); *C07D 307/32* (2013.01)

(58) Field of Classification Search
None
See application file for complete search history.

(56) References Cited

U.S. PATENT DOCUMENTS

| 2,813,900 | A | 11/1957 | Dunlop et al. |
| 3,701,789 | A | 10/1972 | Ramos-Rodriguez |
| 4,533,743 | A | 8/1985 | Medeiros et al. |
| 4,897,497 | A | 9/1990 | Fitzpatrick |
| 5,608,105 | A | 3/1997 | Fitzpatrick |
| 6,617,464 | B2 | 9/2003 | Manzer |
| 2012/0083611 | A1 | 4/2012 | Van Buijtenen et al. |
| 2012/0329981 | A1 | 12/2012 | Castelijns et al. |
| 2013/0168227 | A1 | 7/2013 | Fagan et al. |
| 2015/0080602 | A1 | 3/2015 | Kelly et al. |
| 2016/0076112 | A1 | 3/2016 | Cai et al. |

FOREIGN PATENT DOCUMENTS

| CN | 101805316 A | 8/2010 |
| CN | 102558108 B | 7/2012 |
| CN | 102659723 A | 9/2012 |
| CN | 102617519 B | 8/2014 |
| EP | 2 537 841 A1 | 12/2012 |
| EP | 2 537 840 B1 | 7/2013 |
| WO | WO 89/10362 A1 | 11/1989 |
| WO | WO 2014/176531 A2 | 10/2014 |

OTHER PUBLICATIONS

Finnish Search Report dated Apr. 22, 2016 and, issued by the Finnish Patent and Registration Office in the corresponding Taiwanese Patent Application No. 20156010. (2 pages).
Extended European Search Report dated Feb. 3, 2017, by the European Patent Office in corresponding European Patent Application No. 16204224.6. (11 pages).
Lange et al: "Furfural-A Promising Platform for Lignocellulosic Biofuels", Chemsuschem, vol. 5, No. 1, Jan. 9, 2012 (Jan. 9, 2012), pp. 150-166, XP055338725.
Yan et al. "Synthesis of y-Valerolactone by Hydrogenation of Biomass-derived Levulinic Acid over Ru/C Catalyst" Energy Fuels, 2009, vol. 23, No. 8, pp. 3853-3858.
Chalid et al. "Green polymer precursors from biomass-based levulinic acid", SciVerse ScienceDirect, Procedia Chemistry 4 (2012), pp. 260-267.
Search Report dated Apr. 4, 2016, by the Finnish Patent Office in corresponding Finnish Patent Application No. 20156006. (2 pages).
Farrauto, Robert J., et al., Fundamentals of Industrial Catalytic Processes, pp. 411-421, Blackie Academic & Professional, London, UK, 1997.

*Primary Examiner* — Kamal Saeed
(74) *Attorney, Agent, or Firm* — Buchanan Ingersoll & Rooney PC

(57) ABSTRACT

A process is disclosed for converting levulinic acid to gammavalerolactone with increased selectivity. The process is based on the recognition of the reaction intermediate, 4-hydroxyvaleric acid, and improved conversion thereof.

16 Claims, No Drawings

SELECTIVE PROCESS FOR CONVERSION OF LEVULINIC ACID TO GAMMAVALEROLACTONE

RELATED APPLICATION

This application claims priority under 35 U.S.C. § 119 to Finnish Patent Application No. FI 20156006 filed in Finland on Dec. 23, 2015, the entire content of which is hereby incorporated by reference in its entirety.

FIELD

The disclosure generally relates to conversion of biomass based feedstock into components classifiable as renewable, such as renewable vehicle fuel components. For example, but not exclusively, conversion of levulinic acid to γ-valerolactone is disclosed in a two step process arrangement.

BACKGROUND INFORMATION

Levulinic acid has been identified as a suitable chemical feedstock that can be processed from hexose sugars derived from biomass. Its conversion into γ-valerolactone (gammavalerolactone, GVL) via hydrogenation and ring closure to the lactone is a promising route to the manufacture of renewable components, for various syntheses, to be used as fuel components or for suitable uses as such.

Conversion of levulinic acid to γ-valerolactone has been reported in U.S. Pat. No. 6,617,464B2. Different catalysts able to perform the hydrogenation and ring closure needed for this reaction were studied and compared. The conversions were performed at a high temperature, 215° C.

Another document disclosing a process for conversion of levulinic acid to γ-valerolactone and further to products such as adipic acid and ammonium adipate is EP2537840B1. The conversion was performed at 130° C. in the presence of at least 0.08% water relative to the amount of levulinic acid. Even though results show high selectivity, was the levulinic acid conversion not satisfactory varying between 51-79%.

Chalid et al. (M. Chalid et al., Green polymer precursors from biomass-based levulinic acid, Procedia Chemistry 4 (2012), pages 260-267) have reported a pathway from levulinic acid to various γ-hydroxy-amides for use as polymer precursors. One step in the process therein reported was the biphasic hydrogenation of levulinic acid to γ-valerolactone using homogenous water-soluble Ru-(TPPTS) catalyst. The reaction proceeded through 4-hydroxypentanoic acid (4-hydroxyvaleric acid, 4-HVA) intermediate product, which was not very stable and reacted easily to gammavalerolactone through cyclization reactions. Even though levulinic acid was quickly converted (98%) at 90° C., the ring closure to gammavalerolactone was not complete after 60 min reaction time.

Hence, there still is need to control the reaction pathway and further optimize the yield of gammavalerolactone as end product. A process is disclosed herein for conversion of levulinic acid with better selectivity towards γ-valerolactone. The γ-valerolactone recovery can be improved in the process. The conversion of levulinic acid can be run under process conditions, wherein hydrogenation side products are minimized.

SUMMARY

A process is disclosed for producing gammavalerolactone in a two-stage process, the process comprising: at a first stage, converting levulinic acid with catalytic hydrogenation into 4-hydroxy pentanoic acid and gammavalerolactone; and at a second stage, reacting said 4-hydroxy pentanoic acid into gammavalerolactone under conditions preventing further hydrogenation.

DETAILED DESCRIPTION

The temperatures suggested in the literature provide rapid conversion of levulinic acid into gammavalerolactone. The present inventor has now for the first time reported that already the temperatures above 140° C. produce undesired side products at conditions rich with hydrogen. Hence, the nearly complete conversion of levulinic acid previously reported does not necessarily provide the best yield of gammavalerolactone, since process conditions favor even further hydrogenation reactions. At laboratory conditions these side products might not be interesting or even analyzable, but in the industrial scale they become relevant and there is a need for better selectivity.

According to a first aspect disclosed herein, there is provided a process for producing gammavalerolactone wherein levulinic acid is catalytically converted into gammavalerolactone via reaction route through 4-hydroxy pentanoic acid as intermediate. Said reaction product is further reacted under conditions preventing further hydrogenation to convert remaining 4-hydroxy pentanoic into gammavalerolactone. This combination of conditions provides a selective gammavalerolactone production, wherein the side product formation is diminished.

More specifically, here is provided a process for producing gammavalerolactone which can include:
  converting levulinic acid with catalytic hydrogenation into 4-hydroxy pentanoic acid and gammavalerolactone, and
  reacting said 4-hydroxy pentanoic acid into gammavalerolactone under conditions preventing further hydrogenation.

According to embodiments of the present process the choice of reaction conditions contributes to selectivity. In the catalytic conversion of levulinic acid, i.e. the catalytic hydrogenation, the temperature may be selected to be from 60 to 120° C., preferably for example, from 80 to 110° C. These conditions have now experimentally shown to provide satisfactory levulinic acid conversion, but at the same time very low amounts of unwanted side products.

Catalytic hydrogenation at the first stage sets minimum requirements for conditions for the hydrogenation reaction to take place. However, the present inventor has found, that engineering the conditions at the second stage to prevent further hydrogenation reactions contributes to selectivity and minimizes side reactions related to over-hydrogenation. Since successful hydrogenation requires optimization and control of reaction conditions, the transfer to the second stage may simply be implemented by removal of at least one of parameters needed for hydrogenation to take place.

The present two-step method finds basis on the experimental findings concerning different reaction conditions for each step.

It is essential that the reaction conditions for 4-hydroxy pentanoic acid conversion into gamma valerolactone are capable of preventing hydrogenation reactions. As a reaction step, this is provided by removing at least one parameter relevant to hydrogenation to take place. When all levulinic acid is converted, the selection of reaction conditions at the second stage promotes the last step, the reaction of 4-hydroxy pentanoic acid to gamma valerolactone. At the same time, reactions from 4-hydroxy pentanoic acid and already formed gamma valerolactone to hydrogenated side products thereof are prevented. According to different embodiments, there are several options for providing such conditions and implementing said removal at least one of hydrogenation reaction conditions. According to an exemplary embodiment, the levulinic acid conversion and 4-hydroxy pentanoic acid conversion are run in two different reactors, which preferably follow one another. Process variables in each reactor may be adjusted to provide optimal conditions to first the hydrogenation reaction and then ring closure. According to another embodiment, the two conversions are run in one reactor, but the gas atmosphere includes first hydrogen and after set time is changed into an inert gas. According to third embodiment, the conditions preventing further hydrogenation are provided by lowering pressure after the first step, the levulinic acid conversion.

The conversion of 4-hydroxy pentanoic acid into gammavalerolactone is conducted at a temperature at least 100° C. When no catalyst is used, the temperature 130 to 200° C. and more preferably for example, 150 to 170° C. According to another embodiment process conditions for reacting said 4-hydroxy pentanoic acid into gammavalerolactone include an acidic catalyst. In the presence of catalyst, the temperature for reacting said 4-hydroxy pentanoic acid into gammavalerolactone is from 100 to 150° C. and more preferably from for example 100 to 120° C.

Some embodiments disclosed herein provide further benefits, e.g. the reaction times may be shorter than in prior art processes. Further, less Ru-catalyst may be needed.

Different embodiments will be illustrated or have been illustrated only in connection with some aspects disclosed herein. A skilled person appreciates that any embodiment of an aspect of the inventive features disclosed herein may apply to other aspects disclosed herein.

Levulinic acid production is related to concept of a biorefinery, a facility that integrates biomass conversion processes and equipment to produce fuels, power and chemicals from biomass.

The chemical composition of biomass depends strongly on its source. The most abundant carbohydrate in nature is cellulose. Cellulose is a non-branched water-insoluble polysaccharide consisting of several hundred up to tens of thousands of glucose units. Levulinic acid may be produced from hexose sugars, such as glucose, by acid catalyzed reaction producing one mole of both levulinic and formic acids from one mole of a hexose. Levulinic acid may be used as such for different applications, or further reacted to other bioprecursors or bioproducts.

The reaction of levulinic acid to gammavalerolactone proceeds via 4-hydroxy-valeric acid according to following scheme:

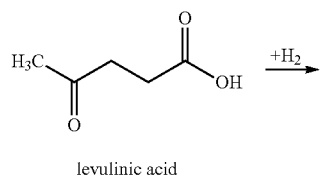
levulinic acid

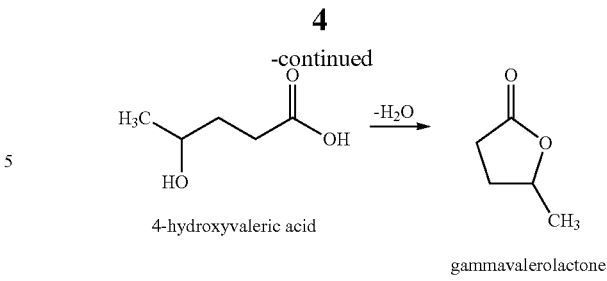
4-hydroxyvaleric acid gammavalerolactone

Even though hydrogenation and ring formation are presented as subsequent reactions, in practice the conversion of levulinic acid easily proceeds to gammavalerolactone. In literature (Chalid), 4-hydroxyvaleric acid has been seen as an unstable intermediate. However, in the present process, the reaction mechanism and control thereon, has been taken into account and process conditions are adjusted respectively. Hence, the present process is also referred to as two-stage process or two-step process, wherein the different requirements of each step may be optimized.

In the present description, the conversion of levulinic acid to 4-hydroxyvaleric acid and to gammavalerolactone, may be referred to as the hydrogenation reaction, first reaction, first stage or the first step. However, the reference should not be understood limiting it to the hydrogenation reaction only, because to those skilled in the art it is well known, that the reaction easily proceeds even to yield gammavalerolactone given the reaction time is sufficiently long. Hence, the reaction product from said levulinic acid conversion includes both gammavalerolactone and 4-hydroxyvaleric acid, wherein the gammavalerolactone typically is the major product. According to the present process, the reaction temperature is chosen sufficiently low to provide a mixture of both said products. According to an embodiment engaging two reactors, the reactor, wherein hydrogenation takes place is referred to as hydrogenation reactor or the first reactor.

It is generally known to those skilled in the art that a hydrogenation reaction to take place sets requirements to reaction conditions. Basically, a H-source is needed, temperature and pressure within a range and catalyst present. Gaseous hydrogen, $H_2$ (g), is mostly used industrially. Alternatively, hydrogen may originate from donor molecules.

Furthermore, heterogenous catalysts are used, for example, in industrial hydrogenations. Heterogenous catalysts provide advantages such as in the stability of catalyst, ease of separation of product from catalyst, a wide range of applicable reaction conditions, and high catalytic ability for the hydrogenation of hard-to-reduce functional groups. Heterogenous commercial catalysts are generally discussed for example in catalyst handbooks. Carbonyl hydrogenation is practiced in both vapor-phase and liquid-phase operations, with liquid-phase being most common for batch processes involving stirred vessels. Adiabatic fixed-bed reactors in series with intermediate cooling or multitubular heat exchange reactors may be used for vapor-phase systems, while trickle adiabatic beds may be employed for liquid carbonyl feed and hydrogen gas fed concurrently. It is advantageous to operate liquid-phase reactors higher pressures to maximize the dissolved $H_2$ in the reactor.

The mechanism of the reaction of levulinic acid into gammavalerolactone via intermediate has been published and the kinetics studied. However, the side reactions occurring besides reaction of 4-HVA to gammavalerolactone has not been studied in detail, because the reaction conditions for converting levulinic acid into gammavalerolactone have, for example, been selected to promote the reaction to proceed completely to gammavalerolactone So far, no need for separate 4-HVA to gammavalerolactone reaction has been recognized.

When referring to the second reaction, second stage or second step, in this description, it concerns the formation of gammavalerolactone from the remainder 4-hydroxyvaleric acid present in the reaction mixture, after substantially all levulinic acid has been converted. According to an embodiment engaging two reactors, the reactor, wherein conditions are selected to prevent hydrogenation to promote the reaction of 4-hydroxyvaleric acid to gammavalerolactone, is referred to as second reactor.

Exceptionally, the second step may be performed to a fraction of the reaction product obtained from the hydrogenation reaction. The benefit of such a reaction is that the majority of the reaction product comprising gammavalerolactone may bypass the second step and smaller reaction equipment is hence needed. The separation or purification needed is nevertheless costly.

Preferably, for example, the reaction product from the first reaction is subjected to the second reaction as such, without separation or purification steps. In such case, the reaction product from the first reaction includes gammavalerolactone as main component, 4-hydroxyvaleric acid as minor component and traces of hydrogenation side products and levulinic acid starting material. Preferably, for example, the amounts of each of said traces is less than 1%-wt and preferably, for example, less than 0.7%-wt and most preferably, for example, less than 0.5%-wt of the total weight of the reaction product from the first reaction. Due to reaction conditions at the second step, the amounts of each of said traces of hydrogenation side products is less than 1%-wt preferably, for example, less than 0.7%-wt, more preferably, for example, less than 0.5%-wt and most preferably, for example, less than 0.1%-wt of the total weight of the reaction product from the second step as well. For example, the amount of 1,4-pentanediol was 0.1%-wt after the first step and within measuring precision, seemed to have further dropped during the second step of the experiment conducted.

The present results taking such small side product amounts into consideration are surprising, since known publications have not discussed their role at all. In the laboratory scale they bear no relevance and in some conditions the concentrations may be too low to easily analyse. However, in industrial scale losses in process yields as well as processing, separating and discharging undesirable side products immediately have effect on the overall economics of the production.

Considering the industrial process, it is essential to convert all levulinic acid to 4-HVA and gammavalerolactone. Those skilled in the art can select process controls to make sure this conversion occurs. Selecting a lower temperature may require longer residence time than higher temperature. However, it has been experimentally shown that temperatures over about 140° C. lead to undesired side product formation under conditions rich with hydrogen and accordingly such conditions are herein avoided. Based on experimental results, the best temperature range for hydrogenation reaction is from 60 to 120° C., preferably, for example, from 80 to 110° C.

The conversion of levulinic acid to 4-HVA and gammavalerolactone is, for example, conducted in the presence of a catalyst. Catalyst suitable for hydrogenation reactions under present conditions, for example, metal. The hydrogenating metal is preferably, for example, selected from metals of the Group VIII of the Periodic Table of Elements, more preferably, for example, Co, Ni, Ru, Pd, and Pt, or a combination thereof. An exemplary catalyst includes Ru-catalyst on a carrier. The catalyst may be selected from carbon-supported or alumina supported ruthenium materials. Commercially available Ru/C catalysts, wherein the ruthenium content is about 1-5%, have experimentally been found suitable. For example, such catalyst is present in the reaction as pellets or other form suitable for heterogenous catalysis in the reactor.

According to exemplary aspects of the present process, the reaction of 4-HVA to gammavalerolactone is performed under conditions preventing further hydrogenation. In practice, preventing further hydrogenation is easiest achieved by removal at least one of hydrogenation reaction conditions needed in first reaction, to react in second reaction said 4-hydroxy pentanoic acid into gammavalerolactone. According to one embodiment, the conditions are provided by conducting the reaction in a second reactor, wherein no hydrogenation takes place. Optionally, the temperature at said second reactor may be higher than in said first reactor, preferably, for example, higher than 140° C., more preferably, for example, from 150 to 200° C. and most preferably, for example, from 150-170° C. However, in case an acid catalyst is used in the second reaction, the temperature may be between 100° C. and 150° C., preferably, for example, between 100° C. and 120° C. The pressure is preferably lower than in the first reactor.

Basically, one means for preventing further hydrogenation reactions is the removal of hydrogenation catalyst, the catalyst of the first stage. Optionally, according to another embodiment, the reaction of 4-HVA to gammavalerolactone may be promoted by use of another catalyst which is suitable for said reaction. Such catalyst may be selected from acidic catalyst, such as IER (ion exchange resin) or zeolite. In embodiments, wherein the reaction of 4-HVA to gammavalerolactone, second reaction, is promoted by use of a catalyst, the temperature may be lower, from 100 to 150° C., preferably, for example, from 100 to 120° C.

According to an embodiment, the conditions preventing further hydrogenation for the conversion of 4-hydroxyvaleric acid to gammavalerolactone are provided by replacing the hydrogen atmosphere with an inert gas atmosphere. Generally, inert gases include the noble gases or gases behaving inertly at the reaction conditions of the present process. Inert gases may include nitrogen, argon, and carbon dioxide or any mixtures thereof, of which preferred are, for example, nitrogen, carbon dioxide or mixtures thereof. The atmosphere may be provided running both said reactions in one reactor or running hydrogenation in first reactor and 4-hydroxyvaleric acid conversion in second reactor. Running both reactions in one reactor provides benefits in batch-wise processes wherein the process equipment is simpler due to changing conditions within one reactor. The atmosphere change may be conducted together with a temperature change, with which the temperature for the second step may be higher than for the first step. Conducting the first and second reactions in different reactors provides benefits especially when the process is run continuously.

The inert gas may be provided as a flow to the reactor. With inert gas flow the reaction from 4-hydroxyvaleric acid to gammavalerolactone may be further promoted in the second step by removal of water during the reaction. Water drawn from the reaction and removed from the reactor shifts the reaction balance to desired direction, to formation of gammavalerolactone. Eventual 4-hydroxyvaleric acid reacting back to levulinic acid is thereby reduced.

According to yet another embodiment, the conditions preventing further hydrogenation for the second reaction are provided by lowering substantially the reactor pressure after said first reaction.

According to another embodiment, the process takes place in a reactor which has been arranged to include two beds, one bed including the Ru-catalyst needed for levulinic acid conversion and the other bed including acidic catalyst to favor the conversion of 4-HVA to gammavalerolactone.

EXPERIMENTAL

The foregoing description provides non-limiting examples of some embodiments disclosed herein. It is clear to a person skilled in the art that the invention is not restricted to details presented, but that the invention can be implemented in other equivalent means and processes. Some of the features of the above-disclosed embodiments may be used to advantage without the use of other features. In the experimental part, especially in tables attached, following references are used: levulinic acid (LA), 4-hydroxyvaleric acid (4-HVA) and gammavalerolactone (GVL).

1 Continuous Process Set-Up to Study the Effect of Different Temperatures to Side Product Formation during Hydrogenation An experiment lasting almost two months was set up to study the effect of temperature on the levulinic acid conversion into gammavalerolactone, 4-hydroxyvaleric acid, and side products. Constant reactor conditions were pressure of 50 bar and contact time with the catalyst as WHSV 1 h$^{-1}$. Levulinic acid was used as feedstock in the experiment to produce gammavalerolactone by hydrogenation over reduction catalyst (2% Ru/C) in a tubular reactor system. The reaction conditions were otherwise kept constant, but the temperature was changed following sequence: 140, 150, 130, 150, 110, 90, 150 and 180° C.

The formation of 4-hydroxyvaleric acid and different side products at various reaction temperatures is shown in Table 1. Values given represent gas chromatography areas (GC-areas) calculated as averages. There, it is clearly seen that at temperatures 90-110° C. the content of any one of the side products did not exceed 1%-wt. However, at higher temperatures, the sum of the side products was increased and the individual contents were higher as well.

More specifically, 1,4-pentanediol and 2-butanol content decreased at lower temperatures (90 and 110° C.). At 180° C. 2-butanol, 2-pentanol, 1-pentanol and 1,4-pentanediol and 2-methyltetrahydrofuran contents clearly increased compared to the lower thermal conditions.

TABLE 1

Detected compound from hydrogenation of LA over Ru/C catalyst at different reaction temperature.

| | Reaction temperature [° C.], GC [area-%] | | | | | |
|---|---|---|---|---|---|---|
| Compounds | 90 | 110 | 130 | 140 | 150 | 180 |
| 2-methyl-THF | 0.0 | 0.0 | 0.1 | 0.3 | 0.2 | 0.7 |
| 2-butanol | 0.0 | 0.0 | 0.1 | 0.4 | 0.2 | 1.5 |
| 2-pentanol | 0.0 | 0.0 | 0.0 | 0.1 | 0.0 | 0.2 |
| GVL | 90.2 | 96.6 | 96.9 | 95.3 | 96.0 | 95.7 |
| 1,4-pentanediol | 0.2 | 0.4 | 1.5 | 2.5 | 1.4 | 0.7 |
| LA | 2.1 | 0.0 | 0.0 | 0.0 | 0.0 | 0.0 |
| 4-HVA | 6.8 | 2.5 | 1.0 | 0.8 | 1.6 | 0.6 |
| Heavy acid | 0.1 | 0.0 | 0.1 | 0.2 | 0.1 | 0.1 |
| Sum | 99.4 | 99.6 | 99.7 | 99.6 | 99.6 | 99.3 |

The test results show that the concentration of 4-hydroxypentanoic acid increases at lower temperatures whereas the concentrations of other side products simultaneously decrease. The explanation is that good selectivity to gammavalerolactone and 4-hydroxyvaleric acid is favored at low temperatures.

2 Batch Experiment Utilizing Levulinic Acid Hydrogenation Product Mixture as the Feed An experiment was set up to provide conditions preventing further hydrogenation, i.e. hydrogen was not present. The reaction was conducted under conditions, wherein the temperature was 150° C., pressure 2-3 bar and no catalyst was present. The effect of the second step of the two-stage process was studied with a batch experiment, wherein a product mixture obtained from levulinic acid conversion was used as the feed. The feed was obtained from reaction described in example 1. The product mixture contained mainly gammavalerolactone and the hydrogenation intermediate 4-hydroxyvaleric acid but also some unreacted levulinic acid. From the gas chromatography (GC) analysis results summarized in table 2 one can conclude that the 4-hydroxyvaleric acid was successfully converted to gammavalerolactone. At the same time the formation of the side products was effectively restricted.

TABLE 2

Results of the second step of the two-stage process.

| Compound | GC area-% Feed | 5 h reaction time |
|---|---|---|
| GVL | 88.9 | 97.3 |
| 1,4-pentanediol | 0.3 | 0.1 |
| Levulinic acid | 1.2 | 1.2 |
| 4-HVA | 8.7 | 0.7 |
| Heavy acid | 0.1 | 0.4 |
| Sum | 99.2 | 99.7 |

The increase in gammavalerolactone is substantially higher compared to the decrease in 4-HVA, indicating that gammavalerolactone could also be formed from some other intermediates than 4-HVA. Giving the results as area-%, it is possible to see that the area-increase of gammavalerolactone is in the same range as the area decrease of 4-HVA.

As such, the foregoing description shall be considered as merely illustrative of the principles of the invention, and not in limitation thereof. Hence, the scope of the invention is only restricted by the appended patent claims.

It will therefore be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

The invention claimed is:

1. A process for producing gammavalerolactone in a two-stage process, the process comprising:
    at a first stage, converting levulinic acid with catalytic hydrogenation into 4-hydroxy pentanoic acid and gammavalerolactone; and
    at a second stage, reacting said 4-hydroxy pentanoic acid into gammavalerolactone under conditions preventing further hydrogenation.

2. The process of claim 1, wherein reaction conditions for reacting said 4-hydroxy pentanoic acid into gammavalerolactone include a temperature of at least 100° C.

3. The process of claim 1, wherein a temperature for reacting said 4-hydroxy pentanoic acid into gammavalerolactone is from 130 to 200° C.

4. The process of claim 1, wherein conditions for reacting said 4-hydroxy pentanoic acid into gammavalerolactone include an acidic catalyst.

5. The process of claim 4, wherein the temperature for reacting said 4-hydroxy pentanoic acid into gammavalerolactone is from 100 to 150° C.

6. The process of claim 1, wherein the reaction conditions at the first stage, for said catalytic hydrogenation of levulinic acid comprise at least one of the following:
temperature from 60 to 120° C.; and
catalyst selected from metals of Group VIII of the Periodic Table of Elements or a combination thereof.

7. The process of claim 6 wherein the catalyst for said catalytic hydrogenation is selected from Co, Ni, Ru, Pd, Pt, or a combination thereof.

8. The process of claim 1, wherein the conditions preventing further hydrogenation at the second stage are provided by running the levulinic acid conversion in a first reactor and 4-hydroxy pentanoic acid conversion in a second reactor.

9. The process of claim 1, wherein the conditions preventing further hydrogenation at the second stage are provided by lowering the hydrogen pressure after the levulinic acid conversion.

10. The process of claim 1, wherein the conditions preventing further hydrogenation at the second stage are provided by running the levulinic acid conversion at hydrogen atmosphere and 4-hydroxy pentanoic acid conversion at an inert gas atmosphere.

11. The process of claim 3, wherein the reaction conditions at the first stage, for said catalytic hydrogenation of levulinic acid comprise at least one of the following:
temperature from 80 to 110° C.; and
catalyst selected from metals of Group VIII of the Periodic Table of Elements or a combination thereof.

12. The process of claim 5, wherein the reaction conditions at the first stage, for said catalytic hydrogenation of levulinic acid comprise at least one of the following:
temperature from 80 to 110° C.; and
catalyst selected from metals of Group VIII of the Periodic Table of Elements or a combination thereof.

13. The process of claim 2, wherein the conditions preventing further hydrogenation at the second stage are provided by running the levulinic acid conversion in a first reactor and 4-hydroxy pentanoic acid conversion in a second reactor.

14. The process of claim 2, wherein the conditions preventing further hydrogenation at the second stage are provided by lowering the hydrogen pressure after the levulinic acid conversion.

15. The process of claim 2, wherein the conditions preventing further hydrogenation at the second stage are provided by running the levulinic acid conversion at hydrogen atmosphere and 4-hydroxy pentanoic acid conversion at an inert gas atmosphere.

16. The process of claim 1 wherein the catalyst for said catalytic hydrogenation is Ru.

* * * * *